United States Patent
Andrews

(12) 
(10) Patent No.: US 6,303,595 B1
(45) Date of Patent: Oct. 16, 2001

(54) USE OF MIRTAZAPINE FOR TREATING SLEEP APNEAS

(75) Inventor: John Stuart Andrews, Schilde (BE)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/554,143

(22) PCT Filed: Nov. 13, 1998

(86) PCT No.: PCT/EP98/07330

§ 371 Date: Jul. 14, 2000

§ 102(e) Date: Jul. 14, 2000

(87) PCT Pub. No.: WO99/25356

PCT Pub. Date: May 27, 1999

(30) Foreign Application Priority Data

Nov. 14, 1997 (EP) .................................. 97203548

(51) Int. Cl.$^7$ .................................... A61K 31/55
(52) U.S. Cl. ............................................ 514/215
(58) Field of Search ..................... 514/214, 215

(56) References Cited

U.S. PATENT DOCUMENTS

| | | | | |
|---|---|---|---|---|
| 4,314,081 | * | 2/1982 | Molloy et al. | 564/347 |
| 5,968,932 | * | 10/1999 | Winokur et al. | 514/227.8 |
| 5,977,099 | * | 11/1999 | Nickolson | 514/214 |
| 6,117,855 | * | 9/2000 | Carlson et al. | 514/90 |

FOREIGN PATENT DOCUMENTS 0 518 767   12/1992   (EP) .

WO 97 22339   6/1997   (WO) .

OTHER PUBLICATIONS

Stimmel et al, Pharmacotherapy, Vo. 17, #1, pp. 10–21 (abstract), Jan. 1997.*
Hanzel et al, Chest, vol. 100, #2, pp. 416–421 (abstract), Aug. 1991.*
Terra, Ann. Pharmacother., vol. 31, #6, pp. 776–768 (abstract), Jun. 1997.*
Carley et al, Am. J. Respir. Crit. Care Med., vol. 160, pp. 1624–1629, 1999.*
Radulovacki et al., "Serotonin 5–HT$_3$–receptor Antagonist GR 38032F Suppresses Sleep Apneas in Rats," Sleep, vol. 21, No. 2, 1998, pp. 131–136.
M.Yoshioka et al., "Pharmacological Characterization of 5–Hydroxytryptamine–Induced Apnea in the Rat," Journal of Pharmacology and Experimental Therapeutics, vol. 260, No. 2, 1992, pp. 917–924.
Th. de Boer, Ph.D, "The Pharmacologic Profile of Mirtazapine," J Clin Psychiatry, 1996:57 (suppl 4), pp. 19–25.
G.L. Stimmel et al., "Mirtazapine: An Antidepressant with Noradrenergic and Specific Serotonergic Effects," Pharmacotherapy, vol. 17, No. 1, 1997, pp. 10–21.
J. Touchon, "Utilisation Des Antidepresseurs Dans Les Troubles Du Sommeil: Considerations Pratiques" L'Encephale, vol. 7, 1995, pp. 41–47 (French).

* cited by examiner

Primary Examiner—James H. Reamer
(74) Attorney, Agent, or Firm—Michael G. Sullivan

(57) ABSTRACT

The compound mirtazapine is found to be effective in treating sleep apneas. Optionally, mirtazapine is combined with an SSRI such as fluoxetin.

7 Claims, No Drawings

USE OF MIRTAZAPINE FOR TREATING SLEEP APNEAS

The present invention pertains to the treatment of sleep apneas. Sleep apnea is defined as the cessation of breathing during sleep. It comprises a spectrum of respiration-related disorders with varying severity and morbidity, involving periods, during sleep, in which airflow is disturbed. The usual classification of sleep apneas distinguishes obstructive, central, and mixed apneas, depending on the presence or absence of respiratory efforts during the periods in which airflow has ceased. In the case of the obstructive sleep apnea syndrome, which is the most familiar apnea, sporadic recurring collapse of the patient's upper airway occurs during sleep. If the collapse is complete, there is no air exchange at the nose and the mouth, and breathing is interrupted. The usual result is a partial arousal from sleep, and a return to normal breathing. The patient in most instances does not have any knowledge or memory of these apnea episodes, but finds himself constantly suffering from fatigue and daytime sleepiness for no apparent reason. These recurrent apnea episodes with resultant hypoxemia and fragmented sleep can have serious neurologic and cardiac consequences. While the obstructive sleep apnea is a physical blockade, central sleep apnea is defined as a neurological disorder, causing cessation of all respiratory effort during sleep, usually with decreases in blood oxygen saturation. The effects of both types of apneas are highly similar. Mixed apnea is a combination of the previous two. An episode of mixed sleep apnea usually starts with a central component and then becomes obstructive in nature.

The sleep apnea syndrome today is regarded as a serious problem, as it occurs widely, and there is a true lack of an effective treatment. Surgical and mechanical interventions have been suggested and tried as treatments, as has oxygen administration during sleep, but none of these are recognised to be very suitable. Pharmacological intervention has also been tried, but with little success. In fact, several kinds of respiratory stimulants, theophylline, antidepressants, and progestogens have been used to treat sleep apneas, but none of these has been found to be very effective.

It is an object of the present invention to provide an effective medicine against sleep apneas. To this end, the invention is a method for the treatment of an animal, for example, a mammal including a human patient, suffering from sleep apnea, comprising administering an effective amount of mirtazapine. The invention also involves the use of mirtazapine for the manufacture of a medicament for the treatment of sleep apnea.

Without wishing to be bound by theory, the applicant, with the hindsight of the unexpected effect of the invention, believes that it is the particular serotonergic profile of mirtazapine which is responsible for the efficacy against sleep apnea.

It should be noted that in a 1992 scientific publication (The Journal of Pharmacology and Experimental Therapeutics, Vol. 260 No. 2, pages 917–924), the pharmacological characterisation of the receptors mediating 5-HT (serotonin)—induced apnea has been investigated by studying the inhibitory effects of exogenous 5-HT on respiration and phrenic nerve activity in anaesthetised rats. This study supports the nowadays recognised potential importance of serotonin receptors in respiration, and indicates, int.al., that 5-HT and 2methyl-5-HT provoked central apneas are antagonised by ondansetron (GR 38032 F), which is a selective $5HT_3$ antagonist.

The invention resides in the finding that an effective medicine against sleep apneas is provided on the basis of the compound mirtazapine. This compound displays a combined serotonergic antagonistic activity to the effect that it simultaneously is a combined 5HT2A, 5HT2C and 5HT3 antagonist. The invention in general pertains to the use of this compound for manufacturing a medicament for treating sleep apneas, Surpisingly, the compound is not only useful as a therapy against sleep apneas of the central type, but also against sleep apneas of the obstructive and mixed types.

Mirtazapine is known, e.g. from U.S. Pat. No. 4,062,848. The compound containing a centre of chirality, it may exist as different enantiomers and enantiomeric mixtures. The present invention includes the use of any particular enantiomer alone, or in a mixture with one or more stereoisomers, in any proportion including racemic mixtures. The present invention includes any salts of the compound, such as acid addition salts, for example, hydrochloric, fumaric, maleic, citric or succinic acid, these acids being mentioned only by way of illustration and without implied limitation. These compounds can be prepared in accordance with U.S. Pat. No. 4,062,848, incorporated herein by reference.

In a preferred embodiment, the aforementioned compound is combined with a selective serotonin reuptake inhibitor (SSRI). SSRI's, and pharmaceutically acceptable salts thereof, are known and have been available since the early 1980s. They include zimelidine, fluoxetine and fluvoxamine. Other SSRI's are for example citalopram, cericlamine, femoxetine, ifoxetine, cyanodothiepin, sertraline, paroxetine, and litoxetine. SSRI's are known to the skilled person, and may be prepared by any method known in the art. For example, fluoxetine or pharmaceutically acceptable salts thereof, can be prepared in accordance with U.S. Pat. No. 4,314,081, incorporated herein by reference.

A further benefit of mirtazapine, is that it also has antidepressant and anxiolytic properties, which helps to overcome secondary symptoms of which sleep apnea patients may suffer. Moreover mirtazapine improves the quality of sleep in general, which up to date has not been achieved with treatments of sleep apnea.

The compounds used according to the invention are to be administered in dosages of from 0.01 to 30 mg per kilogram body weight of the recipient per day, preferably in the range of 0.1 to 5 mg per kg body weight. In most instances, the preferred dosage of mirtazapine is 5 to 45 mg per day, and more preferably 15–30 mg. The SSRI dose may vary depending on the potency and efficacy of the specific active substance, but will generally be in the range of from 5 to 300 mg per day. E.g. citalopram and paroxetine will have a suitable dose of 40–50 mg, while the doses for fluvoxamine and sertraline will be 200–300 mg per day. In general, a suitable dose of an SSRI or a pharmaceutically acceptable salt thereof for administration to a human will be in the range of 0.01 to 50 mg per kilogram body weight of the recipient per day, preferably in the range of 0.1 to 3 mg per kilogram body weight per day. The preferred SSRI is fluoxetine which, administered in a dose within the range of 0.01 to 10 mg per kilogram body weight of the recipient per day, preferably in the range of 0.1 to 1 mg per kilogram body weight per day, together with the above preferred dose of mirtazapine forms the best choice for providing a highly effective medicament for the treatment of sleep apneas of the obstructive and mixed types.

The method of treatment of sleep apneas wherein the compounds according to the invention are administered for therapy to an animal e.g. a mammal including a human, may be carried out in conventional manner, using all kinds of methods, including parenteral, peroral or rectal administration. Administration in the form or oral dosage units, such as tablets or capsules, is preferred. In the method of the invention according to which the aforementioned compounds are used for manufacturing a medicine, the compound can be mixed with all kinds of pharmaceutically acceptable carriers, depending on the method of administration intended. For the preferred, peroral, method of administration, the active compound is taken up in known manner in a composition from which granules or tablets are prepared.

The term "dosage unit" generally refers to physically discrete units suitable as unitary dosages for humans, each containing a predetermined quantity of active material calculated to produce the desired effect, for instance tablets, pills, powders, suppositories, capsules and the like.

Methods and compositions for making such dosage units are well-known to those skilled in the art. For example, conventional techniques for making tablets and pills, containing active ingredients, are described in the standard reference, Gennaro et al., Remington's Pharmaceutical Sciences, (18th ed., Mack Publishing Company, 1990, see especially Part 8: Pharmaceutical Preparations and Their Manufacture). For making dosage units, e.g. tablets, the use of conventional additives, e.g. fillers, colorants, polymeric binders and the like is contemplated. In general any pharmaceutically acceptable additive which does not interfere with the function of the active compounds can be used in the one or more of the compositions.

Suitable carriers with which the compositions can be administered include lactose, starch, cellulose derivatives and the like used in suitable amounts. Lactose is a preferred carrier. Mixtures of carriers can also be used.

The manufacture of the dosage units according to the invention can involve standard pharmaceutical methods known to the skilled person without further elucidation.

TEST EXAMPLE

The efficacy of the compounds according to the invention is tested by studying the effects of administration of mirtazapine (in the range of from 0.05 to 25 mg/kg) in adult Sprague-Dawley rats by monitoring sleep, respiration and blood pressure for a minimum of 6 hours. This follows an accepted physiological animal model (ref. Monti et al., *Pharmacol.Biochem.Behav.*, 51:125–131;1995). The effective suppression by mirtazapine of sleep apneas in the rat model is indicative for similar efficacy in humans.

What is claimed is:

1. A method for the treatment of sleep apneas in an animal, comprising administering a therapeutically effective amount of mirtazapine or a pharmaceutically acceptable salt thereof.

2. The method according to claim 1, further comprising administering a selective serotonin reuptake inhibitor (SSRI).

3. The method according to claim 1, wherein the animal is a human.

4. The method according to claim 1, wherein the SSRI is administered orally.

5. A method for making a medicament for treating sleep apneas, comprising admixing mirtazapine or a pharmaceutically acceptable salt thereof with a pharmaceutically acceptable additive.

6. The method of claim 5, further comprising admixing a selective serotonin reuptake inhibitor (SSRI) with said pharmaceutically acceptable additive.

7. The method of claim 5, wherein said medicament is a dosage unit for oral administration.

* * * * *

UNITED STATES PATENT AND TRADEMARK OFFICE
Certificate

Patent No. 6,303,595 B1                                                                                                 Patented: October 16, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: John Stuart Andrews, Schilde (BE); David W. Carley, Evanston, IL (US); and Miodrag Radulovacki, Chicago, IL (US).

Signed and Sealed this Seventeenth Day of June 2008.

ARDIN MARSCHEL
*Supervisory Patent Examiner*
Art Unit 1614